United States Patent
Kondoh (10) Patent No.: US 8,696,127 B2
(45) Date of Patent: Apr. 15, 2014

(54) OPHTHALMIC APPARATUS

(75) Inventor: Naoyuki Kondoh, Anjo (JP)

(73) Assignee: Nidek Co., Ltd., Gamagori-Shi (JP)

( * ) Notice: Subject to any disclaimer, the term of this patent is extended or adjusted under 35 U.S.C. 154(b) by 219 days.

(21) Appl. No.: 13/176,243

(22) Filed: Jul. 5, 2011

(65) Prior Publication Data

US 2012/0002167 A1 Jan. 5, 2012

(30) Foreign Application Priority Data

Jul. 5, 2010 (JP) .................................. 2010-153470

(51) Int. Cl.
*A61B 3/10* (2006.01)
*A61B 3/103* (2006.01)

(52) U.S. Cl.
CPC ....................... *A61B 3/103* (2013.01)
USPC ......................................................... 351/211

(58) Field of Classification Search
USPC ......................................................... 351/211
See application file for complete search history.

(56) References Cited

U.S. PATENT DOCUMENTS

| | | | |
|---|---|---|---|
| 4,854,692 A | 8/1989 | Kobayashi | |
| 8,079,708 B2 * | 12/2011 | Hamaguchi et al. | .......... 351/205 |

FOREIGN PATENT DOCUMENTS

| | | |
|---|---|---|
| JP | A-64-58237 | 3/1989 |
| JP | A-2006-61461 | 3/2006 |
| WO | WO 2008/062527 A1 | 5/2008 |
| WO | WO 2011/027711 A1 | 3/2011 |

* cited by examiner

*Primary Examiner* — Jack Dinh
(74) *Attorney, Agent, or Firm* — Oliff PLC (57) ABSTRACT

An ophthalmic apparatus includes: a fundus observation optical system for observing a fundus; a target presenting device including a scanning member for two-dimensionally scanning a visible laser beam emitted from a laser source, the device being configured to control emission of the laser source during two-dimensional scanning by the scanning member to project a predetermined target on the fundus under observation through the fundus observation optical system; and control means to change an irradiation diameter of the laser beam by inserting/removing an optical member into/from an irradiation optical path of the laser beam or moving the optical member in an axial direction and to change resolution of the target by changing each scan range of the laser beam by the scanning member according to the changed irradiation diameter of the laser beam. Accordingly, in the ophthalmic apparatus used in close and face-to-face position to an examinee, the size and shape of a target to be presented can be easily set. A test target with high resolution unrealizable by a conventional LCD can be presented.

8 Claims, 5 Drawing Sheets

OPHTHALMIC APPARATUS

CROSS-REFERENCE TO RELATED APPLICATIONS

This application is based upon and claims the benefit of priority from the prior Japanese Patent Application No. 2010-153470, filed on Jul. 5, 2010, the entire contents of which are incorporated herein by reference.

TECHNICAL FIELD

The present invention relates to an ophthalmic apparatus used for examining examinee's eyes.

BACKGROUND ART

Conventional ophthalmic apparatus to be used in a close and face-to-face position to an examinee includes an electronic device such as an LCD (a liquid crystal display). This apparatus is configured to perform observation and photographing of eye fundus through a fundus observation and photographing optical system while having the examinee gaze at a fixation target displayed on the LCD. Further, there is an ophthalmic apparatus adapted to display a visual field test target for visual field test in a position on the LCD other than a position in which the fixation target appears. Thus, a single apparatus can be used for both the fundus photographing and the visual field test which is conducted by finding brightness difference thresholds of visual field test targets in a wide range of a visual field based on responses from an examinee (JP 2006-61461A).

There is further a demand for such an ophthalmic apparatus to display visual-acuity test targets for subjective examination to perform a visual acuity test based on examinee's responses. The LCD is able to form targets having an arbitrary size and an arbitrary shape and thus easily increase the number of types of displayable targets. However, in a visual acuity test needing accurate display of smaller sized targets (targets for high visual acuity) as compared with the targets for visual field test, the resolution of the conventional LCD is insufficient to accurately display the targets for high visual acuity.

The present invention has a purpose to provide an ophthalmic apparatus to be used in a close and face-to-face position to an examinee, the apparatus being capable of easily setting the size and the shape of a target to be presented and presenting a test target with high resolution which is not practicable by a conventional LCD.

DISCLOSURE OF THE INVENTION

Means of Solving the Problems

To achieve the above purpose, one aspect of the invention provides an ophthalmic apparatus comprising: a fundus observation optical system for observing a fundus; a target presenting device including a scanning member for two-dimensionally scanning a visible laser beam emitted from a laser source, the device being configured to control emission of the laser source during two-dimensional scanning by the scanning member to project a predetermined target on the fundus under observation through the fundus observation optical system; and control means to change an irradiation diameter of the laser beam by inserting/removing an optical member into/from an irradiation optical path of the laser beam or moving the optical member in an axial direction and to change resolution of the target by changing each scan range of the laser beam by the scanning member according to the changed irradiation diameter of the laser beam.

MODE FOR CARRYING OUT THE INVENTION

A detailed description of a preferred embodiment of the present invention will now be given referring to the accompanying drawings. The following example exemplifies an ophthalmic apparatus having the function of observing and photographing an eye fundus, the function of measuring a visual field (distribution of sensitivity of vision) based on responses from an examinee, and the function of performing a visual acuity test based on examinee's responses.

Figure 1:
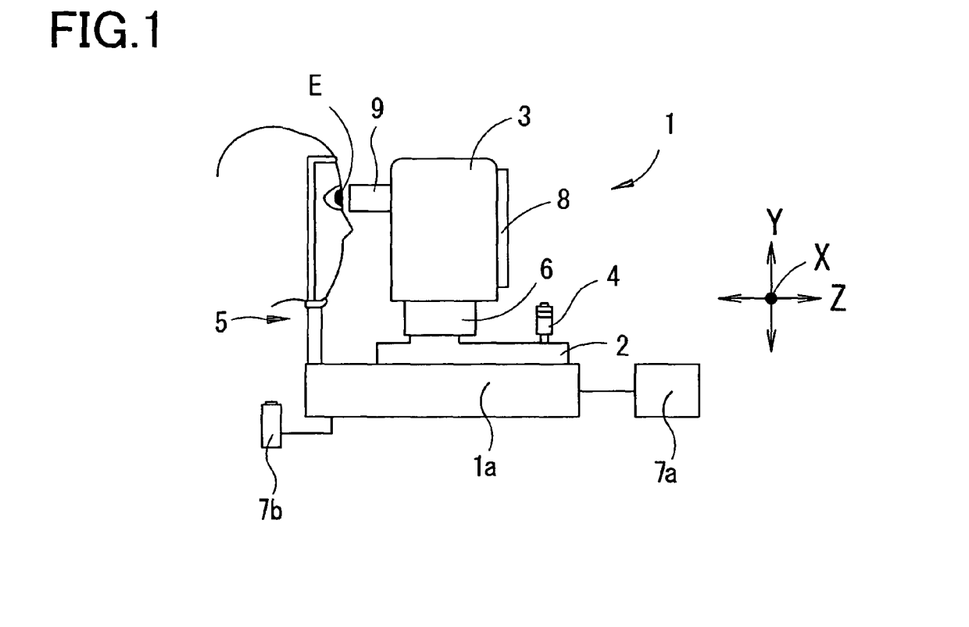
FIG. 1 is an external configuration view of an ophthalmic apparatus.

FIG. 1 is an external perspective view of the ophthalmic apparatus. This apparatus 1 includes a base 1a, a movable table 2 provided to be movable relative to the base 1a in right and left directions (X direction) and back and forth (working distance) direction (Z direction), and a photographing unit (a main unit) 3 provided to be movable relative to the movable table 2 in the right and left direction (X direction), in up and down direction (Y direction), and the back and forth direction (Z direction), and a head supporting unit 5 fixed to the base 1a to support the head of an examinee. The photographing unit 3 contains an optical part mentioned later.

The photographing unit 3 is moved in X, Y, and Z directions (in three-dimensional directions) relative to an examinee's eye E by an electric-powered drive unit 6 provided on the movable table 2. The ophthalmic apparatus 1 further includes a joystick 4 for moving the photographing unit 3 relative to the eye E. When the joystick 4 is tilted, the movable table 2 is slid in the X or Z direction on the base 1a by a sliding mechanism. When a rotary knob (with no reference sign) of the joystick 4 is rotated, the photographing unit 3 is moved in the Y direction by the drive unit 6.

A monitor 8 is provided on an examiner side of the photographing unit 3. The monitor 8 displays a fundus observation screen, an anterior segment observation screen, a visual field test screen, a visual acuity test screen, and so on. The examiner observes the examinee's eye E through the monitor 8. On the examiner side of the photographing unit 3, there is provided a control unit 7a serving as an input unit to set test conditions in various tests and various measuring modes (e.g., a visual acuity measurement mode and a visual field measurement mode) using the ophthalmic apparatus 1. The control unit 7a may be selected from a mouse, a keyboard, a touch panel (attached to the monitor 8), etc. The control unit 7a in this embodiment is also used as an input unit to arbitrarily set the shape and the size of a fixation target, a visual field test target, a visual-acuity test target, and the like and also arbitrarily set the luminance of targets. On the other hand, on the examinee side of the photographing unit 3, there are provided windows 9 through which the examinee peeks during a test and a response button 7b with which the examinee inputs a response signal in the visual field test.

Figure 2:
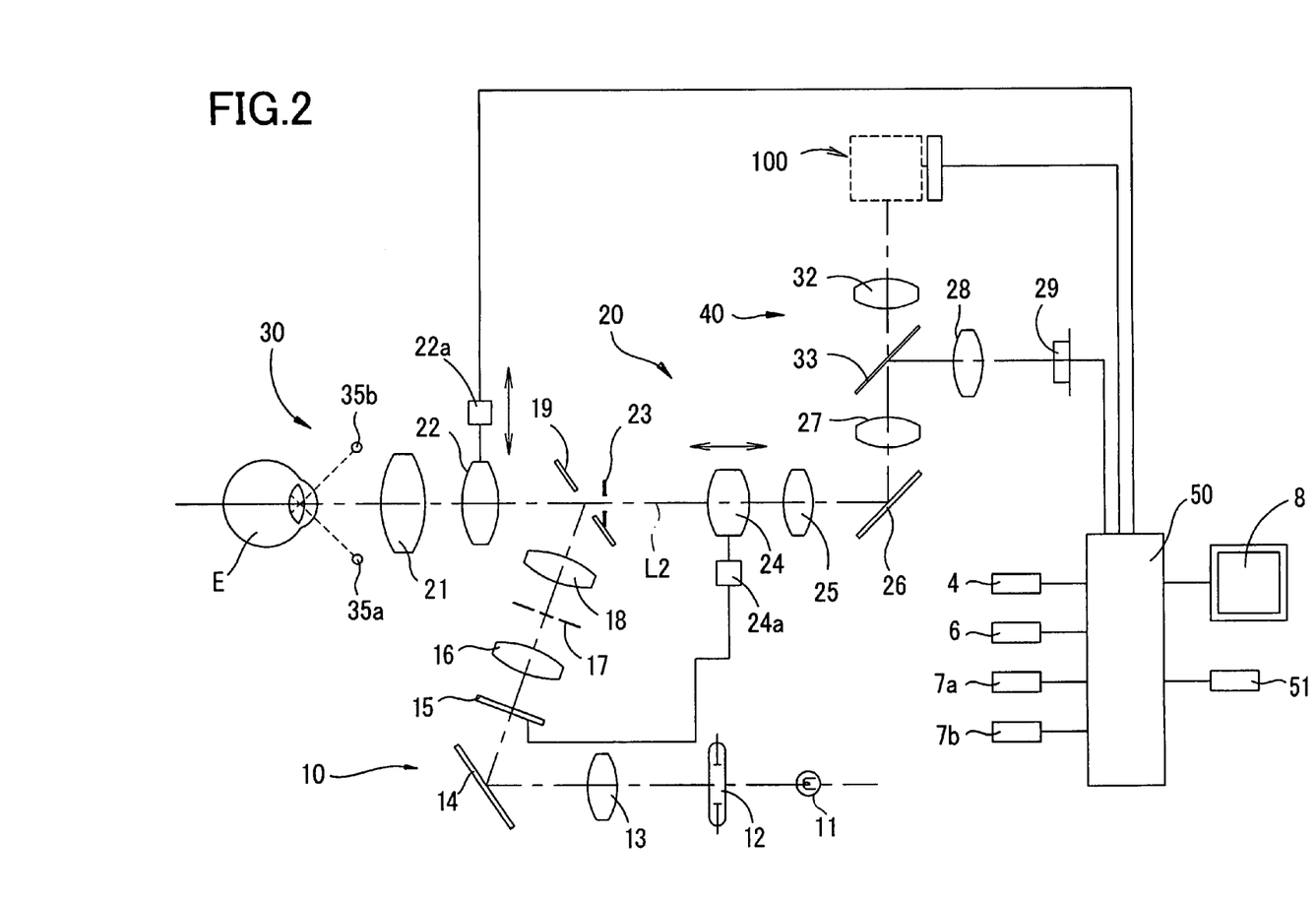
FIG. 2 is a schematic configuration view of an optical system and a control system.

FIG. 2 is a schematic configuration view of optical systems and a control system contained in the photographing unit 3. An optical system 10 for illuminating the fundus of the eye E includes a light source 11 that emits infrared light, a light source 12 that emits flash light in a visible range for photographing the fundus, a collimator lens 13, a total reflection mirror 14, a focus chart 15, a condenser lens 16, a ring slit 17 with a ring-shaped aperture, a relay lens 18, a perforated mirror 19, and an objective lens 21.

The focus chart 15 is a filter having a ring target of a predetermined size. The ring target projected onto the fundus through the focus chart 15 is used as a focus target. The ring target of the focus chart 15 is applied with a coating having the property of transmitting visible light but blocking infrared light. Therefore, when the infrared light source 11 is turned on for fundus observation, a part of the infrared light is blocked off at the position of the ring target and thus the ring target with low luminance is projected onto the fundus. On the other hand, when the visible light source 12 is turned on for fundus photographing, the visible light is transmitted through the entire focus chart 15 including the ring target, thereby illuminating the entire fundus. This focus chart 15 is driven by drive means 24a to move along an optical axis L2 together with a focusing lens 24 mentioned later.

The infrared light emitted from the light source 11 passes through the collimator lens 13 and then illuminates the focus chart 15 from behind. The light from the focus chart 15 forms an image on the fundus through from the relay lens 16 to the objective lens 21. Thus, a ring image is projected onto the fundus. On the other hand, the infrared light passing through the ring slit 17 is reflected by the perforated mirror 19 through the relay lens 18 and then passes through the objective lens 21, forming an image on a pupil of the eye E, thereby illuminating the fundus. The visible light emitted from the light source 12 travels along the same optical path as the infrared light from the light source 11 does and thereby illuminates the fundus. Since the ring target of the focus chart 15 transmits visible light, the visible light emitted from the light source 12 illuminates the fundus uniformly without forming a ring image on the fundus.

A fundus observation and photographing optical system 20 includes the objective lens 21, a photographing diaphragm 23, the focusing lens 24, a relay lens 25, a total reflection mirror 26, a relay lens 27, a beam splitter 33, an imaging lens 28, and a two-dimensional image pickup element 29. The diaphragm 23 is placed in a conjugate position with the pupil of the eye E via the objective lens 21. The focusing lens 24 is moved together with the focus chart 15 along an optical axis L2 by the drive means 24a. The image pickup element 29 has the sensitivity to light from infrared to visible and is located in a conjugate position with the fundus of the eye E. The beam splitter 33 reflects the infrared light from the light source 11 (and infrared light sources 35a and 35b of an anterior segment illumination optical system 30 mentioned later) but transmits the visible light from a target presenting optical system 40 mentioned later. Accordingly, reflection light from the fundus illuminated by the light source 11 passes through from the objective lens 21 to the imaging lens 28 and then is picked up by the image pickup element 29. In addition, a target (a fixation target and a visual field test target in the visual field test and a visual acuity test target in the visual acuity test) formed by the visible light from the target presenting optical system 40 is projected onto the fundus. The beam splitter 33 is switched to a beam splitter (not shown) having the property of transmitting infrared light but reflecting visible light during photographing of the fundus. Thus, the image of the fundus illuminated by the visible light from the light source 12 passes through from the objective lens 21 to the imaging lens 28 and then picked up by the image pickup elements 29.

The anterior segment observation optical system 30 includes the light sources 35a and 35b that emit infrared light, the objective lens 21, and an auxiliary lens 22 for anterior segment observation and shares the optical system consisting of the components from the perforated mirror 19 to the image pickup element 29 with the fundus observation and photographing optical system 20. Herein, a pair of rectangular LEDs is used as the light sources 35a and 35b, which are placed symmetrically with respect to the photographing optical axis L2. An index of diverged light at finity from each of the light sources 35a and 35b is projected toward a cornea at a predetermined projecting angle. These indexes show an alignment state between the eye E and the photographing unit 3 in the three dimensional directions. Further, the entire anterior segment is illuminated by the infrared light sources 35a and 35b.

The auxiliary lens 22 is removably placed on the optical path by drive means 22a consisting of a motor and others. For observation of the anterior segment through the anterior segment observation optical system 30, the auxiliary lens 22 is disposed on the optical axis L2 by actuation of the drive means 22a, providing a conjugate relation between the anterior segment and the image pickup element 29. For fundus observation and photographing, on the other hand, the auxiliary lens 22 is disposed out of the optical path, placing the fundus and the image pickup element 29 in an approximately conjugate relation.

The target presenting optical system 40 includes an imaging lens 32 and a two-dimensional scanning type projector (a target presenting device) 100 and shares the components from the objective lens 21 to the relay lens 27 with the fundus observation and photographing optical system 20.

Figure 3:
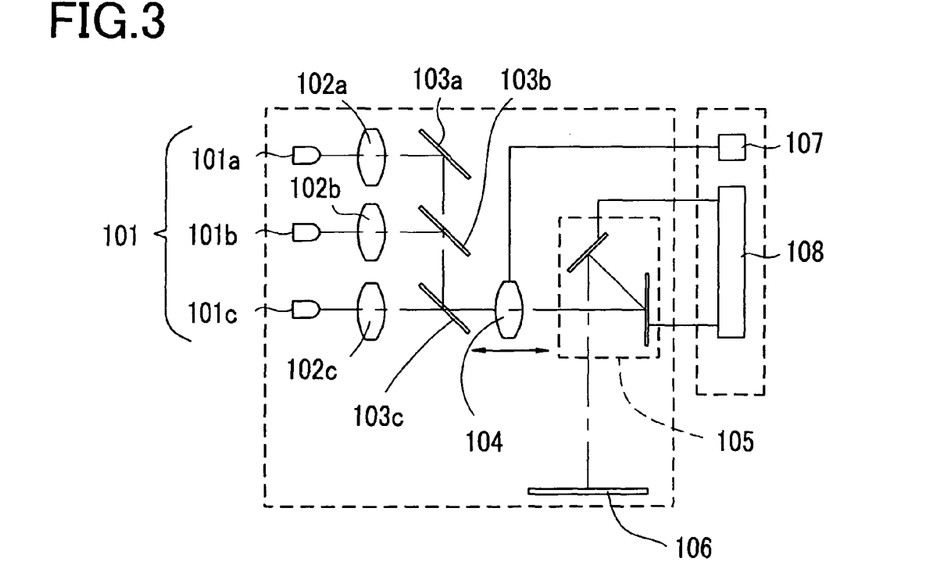
FIG. 3 is an explanatory view showing a configuration of a target presenting device.

FIG. 3 is an explanatory view showing a configuration of the target presenting device 100. This device 100 consists of a visible laser source (hereinafter, "light source") 101 (101a to 101c), collimator lenses 102a to 102c, dichroic mirrors 103a to 103c, a lens (a focusing lens) 104, a scanning member 105, and a screen 106. The visible laser source 101 includes a light source 101a that emits a visible red (R) laser beam, a light source 101b that emits a visible green (G) laser beam, and a light source 101c that emits a visible blue (B) laser beam. Turning-on/off of each light source 101a to 101c is controlled by a controller 50 mentioned later.

The dichroic mirror 103a has the property of reflecting a laser beam emitted from the light source 101a. The dichroic mirror 103b has the property of transmitting a laser beam emitted from the light source 101a but reflecting a laser beam emitted from the light source 101b. The dichroic mirror 103c has the property of reflecting the laser beams emitted from the light sources 101a and 101b but transmitting the laser beam emitted from the light source 101c. The screen 106 is placed in almost conjugate position with the fundus. Accordingly, a projected image (target) on the screen 106 is formed on the fundus via the optical system consisting of the components from the imaging lens 32 to the objective lens 21.

The laser beams emitted respectively from the light sources 101a to 101c are made into parallel luminous fluxes by the collimator lenses 102a to 102c, made coaxial by the dichroic mirrors 103a to 103, and then reflected by the scanning member 105 via the lens 104. The lens 104 is moved in the optical axis direction by actuation of the drive unit 107, thereby changing the beam diameter of a laser beam to be irradiated to the screen 106.

Herein, the lens 104 is moved on the optical path of the laser beam to change the diameter of the laser beam to be irradiated. As an alternative, the irradiation diameter of the laser beam may be changed by inserting/removing an optical member such as a lens into/from the optical path of the laser beam. In the axial movement of the optical member or the insertion/removal of the same, it is preferable to change the irradiation diameter of the laser beam without having an influence on the scan range (angle of view). Therefore, the irradiation diameter of the laser beam and the scan range thereof should preferably be changed separately to enable more appropriate target presentation.

The scanning member 105 consists of two movable mirrors. The laser beam irradiated onto the screen 106 is made to scan two-dimensionally by the scanning member 105 activated by a drive unit 108. Further, the emission timings of the laser beams are controlled according to the scanning timing of the scanning member 105 to form a predetermined target on the screen 106. A scan range and a scan speed of each laser beam by the scanning member 105 is adjusted by the drive unit 108 drivingly controlled by the controller 50 mentioned later.

Figure 4:
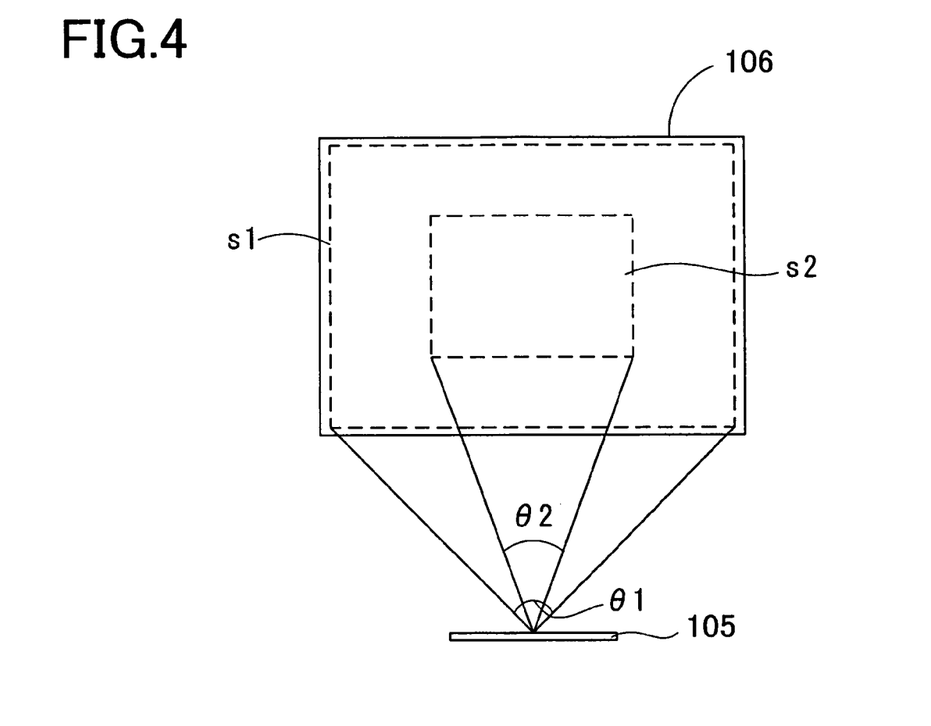
FIG. 4 is an explanatory view showing a relationship between a scan angle and a scan range.

FIG. 4 is an explanatory view showing a relationship between a scan angle of the scanning member 105 consisting of two movable mirrors and a scan range on the screen 106. The screen 106 in the present embodiment is designed with a size corresponding to the angle of view (e.g.,) 45° of the fundus image imaged by the fundus observation and photographing optical system 20. During the visual field test, a scan angle θ1 of the scanning member 105 is set so that the entire screen 106 is used as a display region s1 (a scan region) of a target for visual field test. During the visual acuity test, on the other hand, a scan angle θ2 (smaller than the angle θ1) of the scanning member is set so that a target is presented in a display region s2 (a scan region) narrower than that in the visual field test. In the visual field test, it is unnecessary to accurately present a small target (e.g., a Landolt ring target for a visual acuity 1.5) for use in the visual acuity test. Therefore, the irradiation diameter of the laser beam in the visual field test can be set larger than the irradiation diameter of the laser beam to form a target for visual acuity test.

On the other hand, in the visual acuity test, it is preferable for accurately forming a small target to set a smaller irradiation diameter of the laser beam to be irradiated onto the screen 106 and also set a lower scan speed (movable speed) of the scanning member 105. Accordingly, a target with high resolution can be presented on the screen 106.

The resolution shown in the present embodiment represents the number of pixels included in a predetermined region. The number of pixels is the number of irradiation times (the number of spots) of the laser beam irradiated onto the screen 106 based on the scan speed of the scanning member 105. The resolution of a target in this embodiment is set according to a test mode selected with the control unit 7a. Scanning conditions such as a scan range and a scan speed of the scanning member 105 in the visual field test mode and the visual acuity test mode, the position of the lens 104 (the irradiation diameter of a laser beam), and others are stored as data in advance in a memory 51. The controller 50 retrieves the data on the scanning conditions from the memory 51 based on the selected test mode and applies the retrieved data to the selected test.

The laser beams from the light source 101 are emitted respectively from the R, G, and B light sources 101a to 101c according to inclination angles of the scanning member 105 to thereby form pixels in each color on the screen 106. The scanning by each of the light sources 101a to 101c is repeated in such a manner that, for instance, the laser beam from the light source 101a scans the entire display region s1 first, the laser beam from the light source 101b scans the entire display region s1, and then the laser beam from the light source 101c scans the entire display region s1. When such scanning of the laser beams from the light sources 101a to 101c are repeated in sequence, the pixels of the entire display region s1 are formed without gaps. Further, the scan speed of the scanning member 105 is set to a high speed to such a degree that the projected image (target) in each color on the display region s1 is perceived as a single image superimposed by persistence of vision by an examinee.

A luminous flux from the screen 106 is projected onto the fundus via the imaging lens 32, the lens 27, the mirror 26, the lens 25, the focusing lens 24, the perforated mirror 19, and the objective lens 21. Consequently, the examinee perceives the single image (target) projected onto the screen 106. In the present embodiment, the relay lenses 25 and 27 and the imaging lens 32 constitute a bilateral telecentric system, thereby projecting the luminous flux irradiated from the target presenting device 100 onto the fundus of the eye E uniformly.

In the aforementioned example of the scanning type of the target presenting device 100, the scanning is repeated over the entire display region s1 by each of the light sources 101a to 101c. The output timings of the laser beams from the light source 101 are not limited to the above but may be determined according to the scan angle of the scanning member 105 so that the pixels to be formed by the laser beams output from the light sources 101a to 101c are formed over the entire display region and also the image projected onto the screen 106 is perceivable as a single image by the examinee by persistence of vision. For instance, it may be arranged such that the laser beams from the light sources 101a to 101c are sequentially repeatedly output by one pixel at each scan angle of the scanning member 105 to scan the entire display region s1.

The aforementioned image pickup element 29, the target presenting device 100 (the light source 101 and the drive unit 108), the drive means 22a, and the drive means 24a are connected to the controller 50. This controller 50 detects and processes alignment targets from the anterior segment image picked up by the image pickup element 29 during observation of the anterior segment. During observation of the fundus, furthermore, the controller 50 detects a focus state of the fundus based on the ring target image projected on a retina. The focusing lens 24 is moved along the optical axis L2 by actuation of the drive means 24a to make focus adjustment of the fundus image picked up by the image pickup element 29. The controller 50 controls the output of laser beams from the light source 101 according to the scan speed of the scanning member 105 driven by the drive unit 108.

To the controller 50, additionally, the joystick 4, the drive unit 6, the control unit 7a, the response button 7b, the monitor 8, the memory 51 serving as a storage unit, the light sources 11 and 12, and others are also connected. In the memory 51, there are stored visual-field-test target presenting conditions (target shapes, luminance information, etc.) and visual-acuity-test target presenting conditions (types of test targets such as Landolt rings, visual acuities, etc.). The information in the memory 51 is selected by use of the control unit 7a. The memory 51 stores measurement results obtained in each test.

Operations of the ophthalmic apparatus configured as above will be explained below. In the following case, the visual field test is performed and then the visual acuity test is conducted. When the visual field test mode is selected by operation of the control unit 7a by the examiner, the controller 50 sets a scan angle of the scanning member 105 to the angle θ1 and drives the drive unit 107 to move the lens 104 in the optical axis direction. Thus, the beam diameter of the laser beam to be irradiated onto the entire screen 106 is set larger than that in the visual acuity test mentioned later. The controller 50 switches the display on the monitor 8 to the visual field test screen.

Successively, the examinee is instructed to move his/her head closer to the apparatus 1 and place his/her eye (the eye E) to be photographed in front of the window 9 to peek through the apparatus. From this state, positioning (alignment) using the anterior segment image is performed. The controller 50 drives the drive means 22a to position the auxiliary lens 22 onto the optical axis L2 and turns on the light sources 35a and 35b. The anterior segment of the eye E is thus illuminated and rectangular alignment targets are projected onto the cornea. The controller 50 further drives the target presenting device 100 to present a fixation target to the eye E.

The controller 50 then drives the drive unit 108 to incline the scanning member 105 at a preset scan speed and a preset scan angle. A lower limit of the scan speed of the scanning member 105 is determined to allow the images formed on the screen 106 to be perceived as a single projected image by the examinee and prevent the examiner from feeing flickering. On the other hand, an upper limit is determined to prevent pixels formed on the screen 106 (the display region s1) by scanning from overlapping each other. Accordingly, a clear image is displayed on the screen 106.

The controller 50 drives the drive unit 108 to incline the scanning member 105 in a horizontal direction and make one line scanning of the laser beam in the horizontal direction on the display region s1. At that time, the controller 50 controls turning-on/off of the light source 101 according to the scan speed of the scanning member 105 to thereby output a laser beam in each of R, G, B colors. Specifically, the controller 50 controls the turning-on/off of the light source 101 so the adjacent pixels do not overlap each other and no gap is generated therebetween. The laser beam output from the light source 101 passes through the collimator lenses 102a to 102c, the dichroic mirrors 103a to 103c, and the lens 104 and is reflected by the scanning member 105, and is projected onto the screen 106. Thus, the image formed of the pixels with the size corresponding to the irradiation diameter of the laser beam appears on the screen 106.

Upon completion of scanning in the horizontal direction (one line), the controller 50 controls the drive unit 108 to incline the scanning member 105 slightly (by an amount corresponding to the irradiation diameter of the laser beam) in a vertical direction. Subsequently, scanning is performed in the horizontal direction (one line) in the display region s1. The aforementioned two-dimensional scanning by the scanning member 105 is repeated to form the pixels without gaps in the display region s1.

The controller 50 controls the scan angle of the scanning member 105 and also changes the luminance of the laser beam to be output from the light source 101 according to the scan angle of the scanning member 105. In other words, in a scanning position covering a background part, too, the output of a laser beam is set lower to decrease or darken the luminance of pixels. In contrast, in a fixation target presenting position, the output of a laser beam is set higher to increase or lighten the luminance of pixels. To be concrete, when the controller 50 detects that the scanning position on the screen 106 (the display region s1) by the scanning member 105 reaches the fixation target presenting position on the optical axis L2, the controller 50 increases the output of the laser beam from the light source 101 to thereby increase the luminance of pixels. Thus, a projected image of the fixation target with high (bright) luminance is displayed on the background with low (dark) luminance and in turn the fixation target is projected onto the fundus located in a conjugate position.

Figure 5:
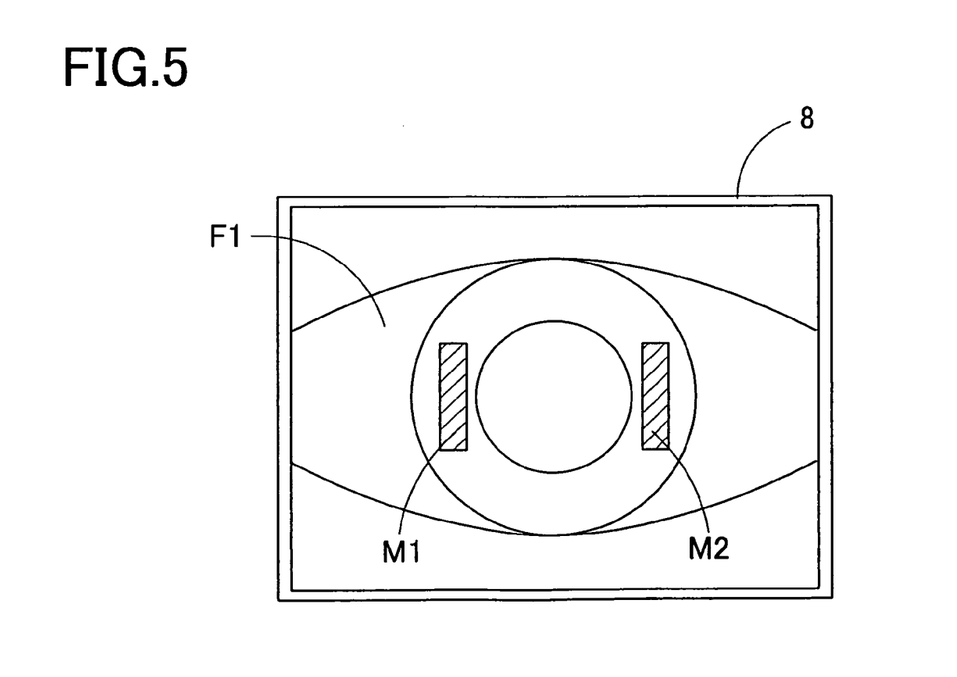
FIG. 5 shows an example of an anterior segment image displayed on a monitor.

As the eye E is guided by the fixation target, the anterior segment image starts to be displayed on the monitor 8. FIG. 5 shows an example of the anterior segment image displayed on the monitor 8. Herein, rectangular alignment targets M1 and M2 appear on the anterior segment image F1 picked up by the image pickup element 29. From this state, the controller 50 performs positioning (alignment) between the photographing unit 3 and the eye E based on light reception results of the alignment targets M1 and M2.

Alignment operations will be explained. The controller 50 drives the drive unit 6 to move and position the entire photographing unit 3 in the up-and-down and right-and-left (X and Y) directions so as to bring a middle point determined from the target images (alignment targets) M1 and M2 detected by the image pickup element 29 into alignment with the pupil center determined from the anterior segment image detected by the image pickup element 29. The controller 50 also drives the drive unit 6 to move and position the entire photographing unit 3 in the back-and-forth (Z) direction relative to the eye E so that the interval between the alignment targets M1 and M2 become a predetermined interval. For the details of the alignment operations, refer to WO2008/062527. When the three-dimensional alignment comes into a permissible range, the controller 50 judges that the alignment is completed and starts focusing of the fundus.

The controller 50 first turns off the light sources 35a and 35b, drives the drive means 22a to move to auxiliary lens 22 out of the optical path, and turns on the light source 11. Further, the controller 50 displays an electronically generated cross-shaped fixation T on the monitor 8 in correspondence with the display position of the fixation target.

Figure 6:
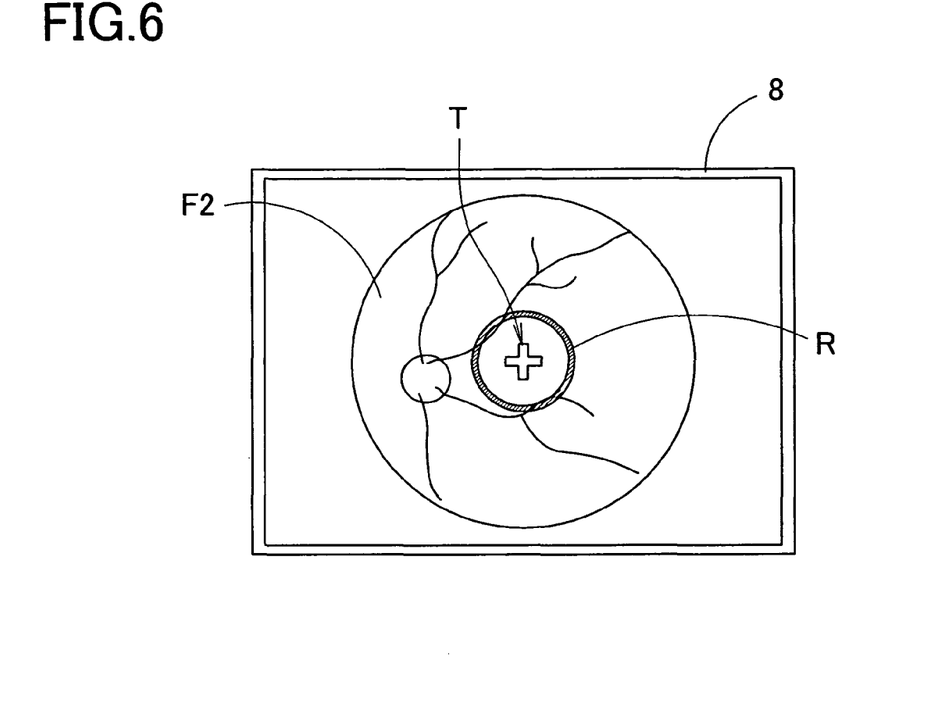
FIG. 6 shows an example of a fundus image displayed on the monitor.

When the reflection light from the fundus illuminated with the infrared light is received by the image pickup element 29, a fundus image appears on the monitor 8. FIG. 6 shows an example of the fundus image displayed on the monitor 8. Herein, a ring target R projected onto the fundus through the focus chart 15 and the electronically-generated fixation target T appear on a fundus image F2. The controller 50 drives the drive means 24a to move the focusing lens 24 until the ring target R comes into focus from an initial light reception state. In the present embodiment, when the ring target R appears with a minimum ring width, it is referred as being in focus. When the controller 50 judges the focus state is appropriate, the focus adjustment is completed.

The examiner then sets tracking to compensate displacement of the presenting position of the target on the fundus caused by rotation of the eye E. The examiner specifies a distinctive point (region) on the fundus displayed on the monitor 8 by operation of the control unit 7a. For instance, a blood vessel or the like is selected as the distinctive point. The controller 50 detects a moving amount of the specified distinctive point on the image pickup element 29 and compensates the presenting position of the target (visual field test target) in alignment with the selected position on the monitor 8 while tracking the motion (movement) of the eye E. Accordingly, the visual field test can be performed accurately at each site of the fundus.

The controller 50 changes the luminance of the pixels in the predetermined position corresponding to each measurement point on the fundus in accordance with a visual field measurement program previously stored in the memory 51, thereby presenting a visual field test target to the eye E. When the controller 50 detects the coincidence of the scanning position in the display region s1 and the presenting position of the visual field test target, the controller 50 controls to increase the output of the laser beams (RGB) to be irradiated from the light source 101 in the same manner of presenting the fixation target as mentioned above to increase the luminance of the pixels. Thereby, only the fixation target and the visual field test target are displayed brightly on the screen 106 by persistence of vision. The projected image on the screen 106 is projected onto the fundus and thus the fixation target and the visual field test target are presented on the fundus. In the present embodiment, the luminance of pixels (brightness of a visual field test target) is changed in 1 dB steps by control of the output of the light source 101 by the controller 50.

Then, the target presenting device 100 is drivingly controlled based on the visual field measurement program to randomly change the presenting position of a visual field test target and change the luminance of the visual field test target. At that time, the examinee who keeps fixation to the fixation target presses the response button 7b if perceives the visual field test target. Based on an input signal, the controller 50 causes the memory 51 to store the luminance of the visual field test target at the time, as response information representing the perceivable sensitivity of the examinee at that measurement point. In the absence of input from the response button 7b with respect to the visual field test target, in contrast, the luminance of the visual field test target at the time is stored in the memory 51 as response information representing the unperceivable sensitivity of the examinee at the measurement point.

Figure 7:
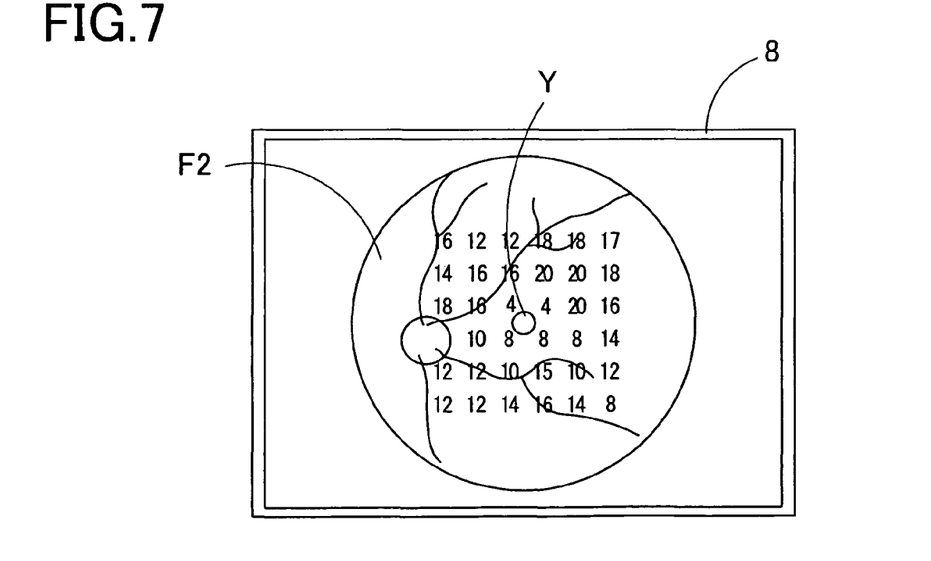
FIG. 7 is a schematic diagram showing distribution of sensitivity of visual field at all measurement points in a visual field test.

After completion of the visual field test at all the measurement points, the controller 50 causes the monitor 8 to display the distribution of sensitivity thresholds of the fundus visual field as shown in FIG. 7. The examiner checks the distribution of visual function on the retina from the distribution of visual field sensitivity displayed on the monitor 8. In the present embodiment, attenuation values of luminance of the visual field test target are used to show the sensitivity distribution. That is, the sensitivity distribution is indicated as a difference from a highest luminance. Therefore, the visual field sensitivity at each site of the retina is regarded as being higher as its value is larger. In FIG. 7, the sensitivity distribution around a macula Y indicates small values. From this result, it is determined that a disease is present near the macula Y of the eye E.

In case any possibility of disease is found near the macula Y from the visual field test results, it is discussed to utilize another site of the fundus of the eye E for a preferred retinal locus (PRL) that is a substitutive portion of the macula. In this case, it is convenient to perform a visual acuity test at the PRL in order to check actual viewing at the selected PRL.

When the visual acuity test mode is selected by operation of the control unit 7a, the controller 50 sets the scan angle of the scanning member 105 to the angle θ2 and drives the drive unit 107 to move the lens 104 in the optical axis direction to thereby set a smaller irradiation diameter of the laser beam to be irradiated on the screen 106 than in the visual field test. Further, the monitor 8 is caused to display the visual acuity test screen. The examiner sets the presenting position of the visual acuity test target on the fundus by operation of the control part 7a. In the present embodiment, the target is generated by scanning conducted by the target presenting device 100. Accordingly, it is only necessary to change the setting of the scan angle (the scan range) for displaying a visual acuity test target and others in any local region of the fundus. In this embodiment, the visual acuity test at the vicinity of the macula Y is first conducted.

After a site of the fundus to be subjected to the visual acuity test is set, the alignment using the anterior segment image and the focusing with the photographing unit 3 using the fundus image of the eye E are performed in the same manner as in the visual field test.

Upon completion of the alignment of the photographing unit 3 and the eye E, the controller 50 projects the visual acuity test target onto the fundus of the eye E. The controller 50, similarly in the visual field test, drives the target presenting device 100 to irradiate the laser beam from the light source 101, and drivingly controls the drive unit 108 to start scanning of the reflection light from the scanning member 105, on the screen 106. At that time, by the controller 50, the irradiation steps (intervals) of the laser beam from the laser source 101 are set in the same steps as in the visual field test and the scan speed of the scanning member 105 is set lower. Accordingly, more pixels are formed with an increased pixel density in a range defined by the scan angle θ2. The visual acuity test target is displayed with high resolution. Therefore, even a visual acuity test target for a high visual acuity (e.g., an acuity of 1.5) which is less easily displayed on the conventional LCD can be displayed more accurately. The irradiation steps of a laser beam in the visual acuity test may be set shorter than those in the visual field test. This allows generation of yet more pixels in the predetermined region and display of a visual acuity test target with higher resolution.

In conjunction with scanning of the reflection light from the scanning member 105, the controller 50 sets a lower output of the laser beam from the light source 101 to darken the luminance of the pixels in other positions (background) than the displaying position of the visual acuity test target in the display region s2. In the target presenting position, the output of a laser beam from the light source 101 is increased to lighten the luminance of the pixels. Accordingly, a white target A2 (e.g., a Landolt ring target) is displayed by persistence of vision on the black (gray) background on the screen 106 and becomes projected onto the fundus of the eye E.

The visual acuity test target may be a black target on a white background. In this case, the output of a laser beam in the positions other than the displaying position of the visual acuity test target is set higher to increase the luminance of pixels whereas the output of a laser beam in the displaying position of the visual acuity test target is set lower to decrease the luminance of pixels.

Figure 8:
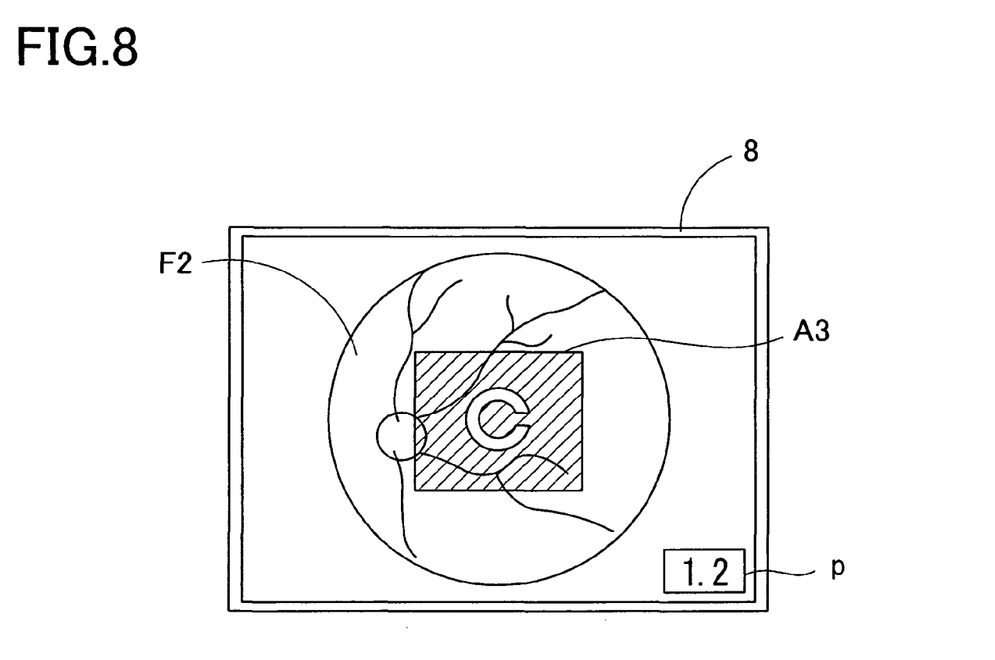
FIG. 8 shows an example of a visual acuity test screen displayed on the monitor.

As shown in an example of the visual acuity test screen in FIG. 8, a target A3 is electronically displayed on the fundus image on the monitor 8 in correspondence with the visual acuity test target appearing in the display region s2. Further, an indication box p is displayed to indicate a visual acuity of the visual acuity test target. This enables the examiner to check the orientation and the visual acuity of the visual acuity test target presented to the eye E.

The examinee to whom the visual acuity test target has been presented makes a verbal response and the like about the orientation of the target. According to the examinee's response, the examiner changes the visual acuity or orientation of the visual acuity test target by operation of the control unit 7a. At that time, since the resolution on the screen 106 has been set higher, even a small visual acuity test target (a visual acuity test target for a high visual acuity) can be accurately presented. Accordingly, the visual acuity test using the visual acuity test targets for various visual acuities is conducted, so that the visual acuity of the fundus site of the examinee can be accurately examined.

In the visual field test, if the retinal sensitivity around the macula Y is found to be low, visual acuities around the macula Y are more likely to be low. The examiner therefore changes the presenting position of the visual acuity test target generated by the target presenting device 100 by operation of the control unit 7a again. For instance, the scan region to be achieved by the target presenting device 100 is set by operation of the control unit 7a based on the visual field test results to present a visual acuity test target in the PRL expected to have a high visual acuity. As above, the use of the target presenting device 100 for forming a target by scanning of the laser beam as mentioned above enables presentation of a target with arbitrary resolution. Further, a target can be generated in an arbitrary position on the fundus by an easier configuration.

The present embodiment exemplifies a configuration that an examiner selects a visual acuity test target based on an examinee's response. As another alternative, the controller 50 may be adapted to automatically switch the visual acuity of a visual acuity test target based on whether a signal input with the response button 7b by an examinee is a correct answer or a wrong answer.

In the ophthalmic apparatus used in a close and face-to-face position to an examinee, as explained above, the target presenting device 100 is used as the target presenting apparatus. Thus, the size and the shape of the target to be presented can be easily set. Further, the test targets with such high resolutions as being unrealizable by the LCD can be presented. The visual acuity test can therefore be performed more accurately. With a single ophthalmic apparatus, both of the visual field test and the visual acuity test can be performed accurately.

In the present embodiment, the scan angle (the range of display region) of the target presenting device 100 is set different between the visual field test and the visual acuity test. Instead of the scan angle, only the irradiation diameter of the laser beam may be set different between the visual field test and the visual acuity test. Specifically, the resolution and the angle of view can be separately adjusted according to the invention and thus more appropriate presentation of a target to the fundus can be realized.

The present embodiment uses the Landolt ring target as the visual acuity test target. Other known targets for visual acuity tests such as E charts can also be displayed with high resolutions. In addition, the visual acuity test can be conducted by preparing visual acuity test targets with any sizes and any shapes by operation of the control unit 7a by the examiner.

Although the present embodiment exemplifies the ophthalmic apparatus, the invention is not restricted thereto. For instance, the invention is applicable to a known fundus camera including a fundus observation and photographing optical system, an ophthalmic photographing apparatus configured to scan a laser beam two-dimensionally on a fundus by a combination of a concave mirror, a galvano mirror, and others and obtain a fundus image by receiving reflection light therefrom, and the like. Various test targets can be thus displayed accurately.

Although the present embodiment shows the configuration that the test target is projected onto the examinee's eye through the screen of the target presenting device, any other configurations may be adopted in which a test target is directly projected on an examinee's eye by use of the target presenting device.

The invention claimed is:

1. An ophthalmic apparatus comprising:
a fundus observation optical system for observing a fundus;
a target presenting device including a scanning member for two-dimensionally scanning a visible laser beam emitted from a laser source, the device being configured to control emission of the laser source during two-dimensional scanning by the scanning member to project a predetermined target on the fundus under observation through the fundus observation optical system; and
control means to change an irradiation diameter of the laser beam by inserting/removing an optical member into/from an irradiation optical path of the laser beam or moving the optical member in an axial direction and to change resolution of the target by changing each scan range of the laser beam by the scanning member according to the changed irradiation diameter of the laser beam.

2. The ophthalmic apparatus according to claim 1, wherein the control means changes the resolution of the target to high resolution by controlling to reduce the irradiation diameter of the laser beam than an irradiation diameter provided before the high resolution is obtained and narrowing a scan range by the scanning member than a scan range provided before the high resolution is obtained.

3. The ophthalmic apparatus according to claim 2, wherein the target presenting device includes a screen on which a target to be formed by the laser beam scanned by the scanning member is projected, the screen being placed in a conjugate position with the fundus through a projection optical system.

4. The ophthalmic apparatus according to claim 3 further including test mode selection means to select between a visual field test mode for testing a visual field of an examinee and a visual acuity test mode for testing a visual acuity of the examinee, and
the control means sets a higher resolution when the visual acuity test mode is selected than when the visual field test mode is selected.

5. The ophthalmic apparatus according to claim 4, wherein the control means changes the resolution of the target to high resolution by controlling the scanning member to narrow an interval of two-dimensional scanning.

6. The ophthalmic apparatus according to claim 5, wherein when the visual acuity test mode is selected by the test mode selection means, the control means sets the scan range by the scanning member according to a size of the target.

7. The ophthalmic apparatus according to claim 6, further including:
a monitor to display the fundus under observation through the fundus observation optical system, and
image processing means to generate an electronic target in a position on the monitor corresponding to a presenting position of the target projected by the visual presenting device.

8. The ophthalmic apparatus according to claim 7, further including target generating means to arbitrarily generate a target to be presented to the examinee's eye.

* * * * *